United States Patent
Li

(10) Patent No.: US 11,857,355 B2
(45) Date of Patent: Jan. 2, 2024

(54) MULTI-DETECTOR SYSTEMS AND METHODS FOR X-RAY IMAGING

(71) Applicant: WISCONSIN ALUMNI RESEARCH FOUNDATION, Madison, WI (US)

(72) Inventor: Ke Li, Middleton, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 68 days.

(21) Appl. No.: 17/514,287

(22) Filed: Oct. 29, 2021

(65) Prior Publication Data

US 2023/0132544 A1   May 4, 2023

(51) Int. Cl.
| | | |
|---|---|---|
| A61B 6/00 | (2006.01) | |
| G06T 11/00 | (2006.01) | |
| G01T 1/17 | (2006.01) | |
| A61B 6/03 | (2006.01) | |

(52) U.S. Cl.
CPC ............ *A61B 6/4266* (2013.01); *A61B 6/032* (2013.01); *A61B 6/4233* (2013.01); *A61B 6/4241* (2013.01); *A61B 6/4435* (2013.01); *A61B 6/54* (2013.01); *G01T 1/17* (2013.01); *G06T 11/005* (2013.01); *G06T 11/008* (2013.01)

(58) Field of Classification Search
CPC ..... A61B 6/032; A61B 6/4233; A61B 6/4234; A61B 6/4241; A61B 6/4266; A61B 6/54; G01T 1/17; G06T 11/005; G06T 11/008
See application file for complete search history.

(56) References Cited

U.S. PATENT DOCUMENTS

| | | | | |
|---|---|---|---|---|
| 11,517,274 | B2 | 12/2022 | Li | |
| 2008/0099689 | A1* | 5/2008 | Nygard | G01T 1/2018 250/370.09 |
| 2010/0034353 | A1* | 2/2010 | Kravis | G01V 5/0025 378/87 |
| 2010/0102242 | A1* | 4/2010 | Burr | G01T 1/20 250/363.01 |
| 2013/0251097 | A1* | 9/2013 | Zou | A61B 6/4266 378/19 |

(Continued)

OTHER PUBLICATIONS

Krüger, H. et al., "CIX: a detector for spectrally enhanced x-ray imaging by simultaneous counting and integrating", 2008, Proc. SPIE 6913, Medical Imaging 2008: Physics of Medical Imaging, 69130P (Year: 2008).*

(Continued)

*Primary Examiner* — Blake C Riddick
(74) *Attorney, Agent, or Firm* — Quarles & Brady LLP

(57) ABSTRACT

A system and method for detection of x-rays is provided. An x-ray detector system may include an energy-integrating x-ray detector having an array of x-ray sensing elements that are configured to sense x-rays emitted from an x-ray source and generate energy-integrating x-ray data. The system may also include a photon-counting detector having another array of x-ray sensing elements configured to determine an interaction between individual x-ray photons with individual sensing elements of the another array of x-ray sensing elements to generate photon-counting x-ray data. The system may further include electronics configured to receive the energy-integrating x-ray data and the photon-counting x-ray data simultaneously.

15 Claims, 7 Drawing Sheets
(2 of 7 Drawing Sheet(s) Filed in Color)

(56) References Cited

U.S. PATENT DOCUMENTS

| | | | | |
|---|---|---|---|---|
| 2013/0284940 | A1* | 10/2013 | Herrmann | G01T 1/17 250/336.1 |
| 2015/0043796 | A1* | 2/2015 | Rigie | G06T 11/005 382/131 |
| 2015/0178958 | A1* | 6/2015 | Zou | A61B 6/4241 378/19 |
| 2015/0223766 | A1* | 8/2015 | Besson | A61B 6/4241 378/62 |
| 2016/0128650 | A1* | 5/2016 | Wang | G06T 11/005 378/5 |
| 2016/0203620 | A1* | 7/2016 | Zou | A61B 6/4241 378/19 |
| 2016/0242725 | A1* | 8/2016 | Wang | A61B 6/4233 |
| 2017/0086762 | A1* | 3/2017 | Kawata | G01T 1/2985 |
| 2017/0212250 | A1* | 7/2017 | Jin | G01T 1/2018 |
| 2018/0364373 | A1* | 12/2018 | Hondongwa | G01T 1/2018 |
| 2021/0239856 | A1* | 8/2021 | Sjölin | G01T 1/247 |
| 2022/0028127 | A1* | 1/2022 | Daerr | A61B 6/4241 |

OTHER PUBLICATIONS

Feng M., X. Ji, R. Zhang, K. Treb, A. M. Dingle, and K. Li, "An experimental method to correct low-frequency concentric artifacts in photon counting CT," Phys. Med. Biol., vol. 66, pp. 175011, 2021.

Ji et al., "Development of an integrated C-arm interventional imaging system with a strip photon counting detector and a flat panel detector", Downloaded on Sep. 27, 2021 at 20:12:59 UTC from IEEE Xplore.

Nagesh et al., "High-Definition Zoom Mode, a High-Resolution X-Ray Microscope for Neurointerventional Treatment Procedures: A Blinded-Rater Clinical-Utility Study", AJNR Am J Neuroradiol (2019).

Treb et al., "Photon counting-energy integrating hybrid at panel detector systems for image-guided interventions: An experimental proof-of-concept", (2023) Phys. Med. Biol. 68 135009.

Treb et al., "A C-arm-mounted Dagger (†) Photon Counting Detector System for both 2D and 3D Interventional Imaging", SPIE Medical Imaging Conference. (2022).

* cited by examiner

MULTI-DETECTOR SYSTEMS AND METHODS FOR X-RAY IMAGING

CROSS-REFERENCE TO RELATED APPLICATIONS

Not applicable.

STATEMENT REGARDING FEDERALLY SPONSORED RESEARCH

Not applicable.

BACKGROUND

Interventional radiology procedures, or image-guided interventions (IGIs), are minimally invasive procedures conducted in an interventional radiology suite. Typical interventional radiology suites are equipped with C-arm x-ray systems that allow the interventional radiologist (or other practitioner) to acquire images during the interventional procedure by rotating the source and detector about the patient using the C-arm. Examiners of interventional radiology procedures include routine procedures such as angioplasties, stent placements, coil embolization, mechanical thrombectomy, liver tumor ablations, rental artery angioplasties, etc., and potentially lifesaving procedures that can include the treatment of intracranial hemorrhages, ischemic strokes, aneurysms, arteriovenous malformations, and so on.

While these C-arm x-ray systems are the typical choice for conducting interventional radiology procedures, they have limited capabilities compared to, for example, diagnostic, fixed-gantry computed tomography (CT) systems. This is generally because the C-arm systems compromise speed and sophistication available in fixed-gantry CT systems in favor of the openness/accessibility and flexibility provided by the C-arm architecture. That is, in an interventional suite, access to the patient is a necessity and the C-arm architecture and systems provide that access, despite requiring compromises relative to the capabilities of fixed-gantry CT systems.

For example, typical C-arm x-ray systems utilize flat panel detectors (FPDs) that operate as energy-integrating detectors (EIDs), which generate a signal proportional to the total energy deposited by all photons without specific information about an individual photon or its energy. Conventional FPDs lack spectral and quantitative imaging capabilities much desired by physicians. Taking radiofrequency ablation therapy for liver metastasis as an example, if high-quality iodine material CT images are available in the interventional room immediately after the ablation, physicians can better determine whether additional ablations need to be performed to achieve a complete ablation with sufficient safety margins. Another example is the differentiation between iodine staining and true bleeding during interventional procedures: both the iodine and bleed can be hyperattenuating on conventional FPD-based CT images. In contrast, iodine material CT images, if available, can help physicians better differentiate between the two.

Thus, it would be desirable to provide systems and methods for x-ray systems that are able to provide greater features and sophistication of imaging capabilities over traditional systems.

SUMMARY OF THE DISCLOSURE

The present disclosure provides systems and methods that overcome the aforementioned drawbacks by providing systems and methods for integrating multiple detectors to provide the user with the advantages of both FPDs and photon counting detectors (PCDs). Systems and methods are also provided for integrating the data from the multi-detector systems. Such multi-detector systems are designed to allow both FPDs and PCDs to acquire x-rays simultaneously.

In some aspects of the disclosure, an x-ray imaging system is provided that includes a gantry configured rotate about a pivot axis and an x-ray source coupled to the gantry and configured to emit x-rays along a path extending to define an axial axis. The system also includes an x-ray detector system coupled to the gantry and configured to receive x-rays traveling from the x-ray source along the path. The x-ray detector includes an energy-integrating x-ray detector having an array of x-ray sensing elements that are configured to sense x-rays emitted from the x-ray source and a photon-counting detector having another array of x-ray sensing elements configured to determine an interaction between individual x-ray photons from the x-ray source and individual sensing elements of the another array of x-ray sensing elements. Both the energy-integrating detector and the photon-counting detector are configured to receive the x-rays emitted from the x-ray source simultaneously.

In another aspect of the disclosure, a method is provided for controlling an x-ray imaging system that includes a gantry, an x-ray source coupled to the gantry, and a multi-detector assembly having an energy-integrating detector array and a photon-counting detector array. The method includes operating the x-ray source to direct x-rays to the multi-detector assembly and acquiring energy-integrating x-ray imaging data in response to receiving the x-rays at the energy-integrating detector array. The method also includes simultaneously with receiving the x-rays at the energy-integrating detector array, acquiring photon-counting x-ray imaging data in response to receiving the x-rays at the photon-counting detector array and reconstructing an image of the subject using at least one of the energy-integrating x-ray imaging data or the photon-counting x-ray imaging data.

In still another aspect of the disclosure, an x-ray detector system is provided that includes an energy-integrating x-ray detector having an array of x-ray sensing elements that are configured to sense x-rays emitted from an x-ray source and generate energy-integrating x-ray data and a photon-counting detector having another array of x-ray sensing elements configured to determine an interaction between individual x-ray photons with individual sensing elements of the another array of x-ray sensing elements to generate photon-counting x-ray data. The system also includes electronics configured to receive the energy-integrating x-ray data and the photon-counting x-ray data simultaneously.

The foregoing and other aspects and advantages of the disclosure will appear from the following description. In the description, reference is made to the accompanying drawings which form a part hereof, and in which there is shown by way of illustration a preferred configuration of the disclosure. Such configuration does not necessarily represent the full scope of the disclosure, however, and reference is made therefore to the claims and herein for interpreting the scope of the disclosure.

BRIEF DESCRIPTIONS OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
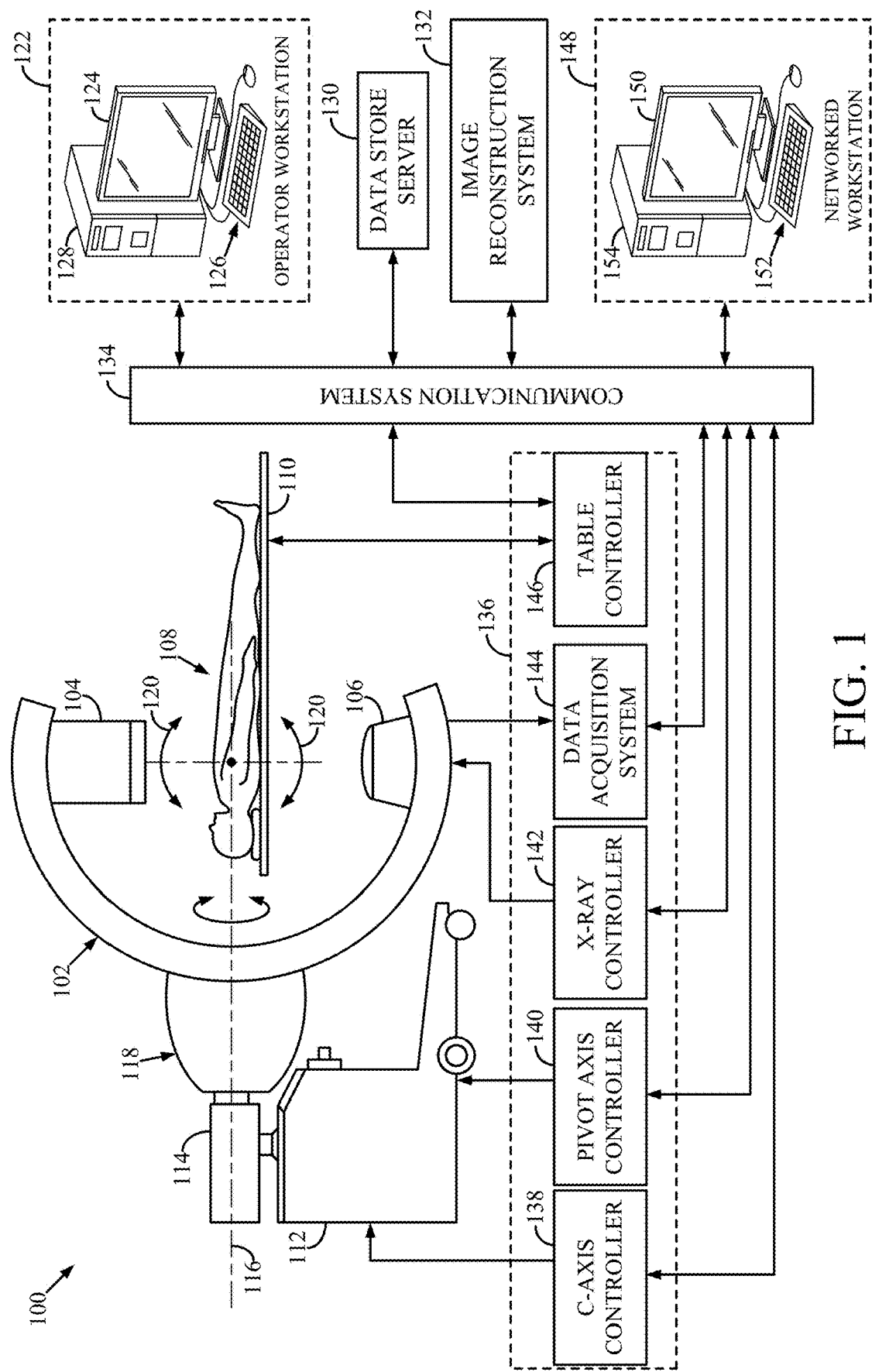
FIG. 1 is a block diagram of an exemplary x-ray imaging system in accordance with the present disclosure.

As detailed above, typical C-arm x-ray systems have an energy-integrating x-ray detector in a flat-panel detector (FPD) geometry. While these energy-integrating x-ray detectors can be particularly well-suited for some imaging tasks, such as, during fluoroscopy, for digital subtraction angiography (DSA) sequences, and for three-dimensional (3D) cone beam computed tomography (CBCT) acquisitions, these energy-integrating FPDs can be ill-suited for other imaging tasks. For example, energy-integrating x-ray detectors are particularly insufficient for procedures that require superior low-contrast detectability, or high spatial resolution (e.g., at least due to the relatively bigger pixel element sizes) or quantitative material (e.g. iodine) information.

Another type of x-ray detector is a photon-counting detector, which is typically implemented with a conventional CT scanner having a bore that houses an x-ray source and detector assembly (e.g., that both rotate around a single axis of rotation). Photon-counting detectors are different than energy-integrating x-ray detectors in that they can spatially discriminate individual x-ray photons (emitted from the x-ray source) generating signals that are proportional to the energy of the x-ray photon. In other words, individual sensors (e.g., pixel elements) of the photon-counting detector can determine individual x-ray photons and their corresponding energies. Conversely, for energy-integrating x-ray detectors, a given x-ray photon that is directed at a given individual sensor (e.g., a pixel element) of the energy-integrating x-ray detector is sensed as a peak in time, with the given x-ray photon possibly also being sensed (partially) by adjacent sensors (e.g., from the given x-ray photon being absorbed by the scintillator and remitted in all directions as light sensed by the sensors). Thus, due to the ability of individual x-ray photon discrimination for the photon-counting detectors, the size of individual sensors can be reduced, which can greatly improve image resolution to effectively discern small structures of a subject when utilizing x-ray photon-counting detectors.

Although some conventional CT scanners have adopted photon-counting detectors, photon-counting detectors have not been widely adopted in interventional radiology suites. For example, while photon-counting detectors have better spatial resolution than energy-integrating x-ray detectors, the energy-integrating x-ray detectors are generally better for a greater number of different imaging tasks than the photon-counting detectors (e.g., at least due to the greater sensitivity of the energy-integrating x-ray detectors). So, many interventional radiology suites being able to only have a single x-ray system (e.g., due to cost constraints) prefer to have the energy-integrating x-ray detector system. As another example, some imaging tasks require a cone beam CT (e.g., for a 3D image acquisition). This would then require replacing the energy-integrating x-ray detector with a photon-counting detector of a similar spatial footprint, which would be far more costly. Thus, at least due to costs, and the decrease in quality (or inability) to complete particular imaging tasks, interventional x-ray systems have not adopted the photon-counting x-ray detectors.

Recognizing these drawbacks, and in an effort to bring spectral imaging to C-arm systems, U.S. application Ser. No. 16/890,960 provides systems and methods to provide energy-resolving photon counting detectors (PCDs) in the C-arm gantry environment, a cost-effective and flexible manner. The PCD provides adequate coverage along both axial (x-y) and z-directions. While facilitating retrofitting to existing systems and being comparatively cost-effective to having two different systems, the additional PCD detector does add cost, as well as some technical issues, such as scatter-induced quantification inaccuracies.

As will be described herein, the present disclosure provides systems and methods for a multi-detector system. In one non-limiting example, a PCD design having a limited footprint that may be tailored specifically for particular clinical applications, such as minimally invasive image-guided interventions (IGI), can be used. The PCD design may be formed by two or more PCD modules to make a multi-detector system. Additionally or alternatively, the PCD may be integrated with a FPD having a different footprint. Systems and methods are provided for integrating and producing any of a variety of images and other clinically-relevant reports from the multi-detector system.

In the non-limiting example of FIG. 1, a CT x-ray imaging system 100 is shown. The illustrated non-limiting example is a "C-arm" that includes a gantry 102 having a C-arm to which an x-ray source assembly 104 is coupled on one end and an x-ray detector array assembly 106 is coupled at its other end. However, the systems and methods provided herein may be likewise use with traditional diagnostic CT systems that have closed gantries or bores. Regardless of the gantry geometry, the gantry 102 enables the x-ray source assembly 104 and detector array assembly 106 to be oriented in different positions and angles around a subject 108, such as a medical patient or an object undergoing examination that is positioned on a table 110. When the subject 108 is a medical patient, this configuration enables a physician access to the subject 108.

The x-ray source assembly 104 includes at least one x-ray source that projects an x-ray beam, which may be a fan-beam or cone-beam of x-rays, towards the x-ray detector array assembly 106 on the opposite side of the gantry 102. The x-ray detector array assembly 106 includes at least one x-ray detector, which may include a number of x-ray detector elements. Examples of x-ray detectors that may be included in the x-ray detector array assembly 106 include flat panel detectors, such as so-called "small flat panel" detectors, in which the detector array panel may be around centimeters in size. Such a detector panel allows the coverage of a field-of-view of approximately twelve centimeters.

Together, the x-ray detector elements in the one or more x-ray detectors housed in the x-ray detector array assembly 106 sense the projected x-rays that pass through a subject 108. Each x-ray detector element produces an electrical signal that may represent the intensity of an impinging x-ray beam and, thus, the attenuation of the x-ray beam as it passes through the subject 108. In some configurations, each x-ray detector element is capable of counting the number of x-ray photons that impinge upon the detector. During a scan to acquire x-ray projection data, the gantry 102 and the components mounted thereon rotate about an isocenter of the C-arm x-ray imaging system 100.

The gantry 102 includes a support base 112. A support arm 114 is rotatably fastened to the support base 112 for rotation about a horizontal pivot axis 116. The pivot axis 116 is aligned with the centerline of the table 110 and the support arm 114 extends radially outward from the pivot axis 116 to support a C-arm drive assembly 118 on its outer end. The C-arm gantry 102 is slidably fastened to the drive assembly 118 and is coupled to a drive motor (not shown) that slides the C-arm gantry 102 to revolve it about a C-axis, as indicated by arrows 120. The pivot axis 116 and C-axis are orthogonal and intersect each other at the isocenter of the C-arm x-ray imaging system 100, which is indicated by the black circle and is located above the table 110.

The x-ray source assembly 104 and x-ray detector array assembly 106 extend radially inward to the pivot axis 116 such that the center ray of this x-ray beam passes through the system isocenter. The center ray of the x-ray beam can thus be rotated about the system isocenter around either the pivot axis 116, the C-axis, or both during the acquisition of x-ray attenuation data from a subject 108 placed on the table 110. During a scan, the x-ray source and detector array are rotated about the system isocenter to acquire x-ray attenuation projection data from different angles. By way of example, the detector array is able to acquire thirty projections, or views, per second.

The C-arm x-ray imaging system 100 also includes an operator workstation 122, which typically includes a display 124, one or more input devices 126, such as a keyboard and mouse, and a computer processor 128. The computer processor 128 may include a commercially available programmable machine running a commercially available operating system. The operator workstation 122 provides the operator interface that enables scanning control parameters to be entered into the C-arm x-ray imaging system 100. In general, the operator workstation 122 is in communication with a data store server 130 and an image reconstruction system 132. By way of example, the operator workstation 122, data store sever 130, and image reconstruction system 132 may be connected via a communication system 134, which may include any suitable network connection, whether wired, wireless, or a combination of both. As an example, the communication system 134 may include both proprietary or dedicated networks, as well as open networks, such as the internet.

The operator workstation 122 is also in communication with a control system 136 that controls operation of the C-arm x-ray imaging system 100. The control system 136 generally includes a C-axis controller 138, a pivot axis controller 140, an x-ray controller 142, a data acquisition system ("DAS") 144, and a table controller 146. The x-ray controller 142 provides power and timing signals to the x-ray source assembly 104, and the table controller 146 is operable to move the table 110 to different positions and orientations within the C-arm x-ray imaging system 100.

The rotation of the gantry 102 to which the x-ray source assembly 104 and the x-ray detector array assembly 106 are coupled is controlled by the C-axis controller 138 and the pivot axis controller 140, which respectively control the rotation of the gantry 102 about the C-axis and the pivot axis 116. In response to motion commands from the operator workstation 122, the C-axis controller 138 and the pivot axis controller 140 provide power to motors in the C-arm x-ray imaging system 100 that produce the rotations about the C-axis and the pivot axis 116, respectively. For example, a program executed by the operator workstation 122 generates motion commands to the C-axis controller 138 and pivot axis controller 140 to move the gantry 102, and thereby the x-ray source assembly 104 and x-ray detector array assembly 106, in a prescribed scan path.

The DAS 144 samples data from the one or more x-ray detectors in the x-ray detector array assembly 106 and converts the data to digital signals for subsequent processing. For instance, digitized x-ray data is communicated from the DAS 144 to the data store server 130. The image reconstruction system 132 then retrieves the x-ray data from the data store server 130 and reconstructs an image therefrom. The image reconstruction system 132 may include a commercially available computer processor, or may be a highly parallel computer architecture, such as a system that includes multiple-core processors and massively parallel, high-density computing devices. Optionally, image reconstruction can also be performed on the processor 128 in the operator workstation 122. Reconstructed images can then be communicated back to the data store server 130 for storage or to the operator workstation 122 to be displayed to the operator or clinician.

The C-arm x-ray imaging system 100 may also include one or more networked workstations 148. By way of example, a networked workstation 148 may include a display 150, one or more input devices 152, such as a keyboard and mouse, and a processor 154. The networked workstation 148 may be located within the same facility as the operator workstation 122, or in a different facility, such as a different healthcare institution or clinic.

The networked workstation 148, whether within the same facility or in a different facility as the operator workstation 122, may gain remote access to the data store server 130, the image reconstruction system 132, or both via the communication system 134. Accordingly, multiple networked workstations 148 may have access to the data store server 130, the image reconstruction system 132, or both. In this manner, x-ray data, reconstructed images, or other data may be exchanged between the data store server 130, the image reconstruction system 132, and the networked workstations 148, such that the data or images may be remotely processed by the networked workstation 148. This data may be exchanged in any suitable format, such as in accordance with the transmission control protocol ("TCP"), the Internet protocol ("IP"), or other known or suitable protocols.

Figure 2:
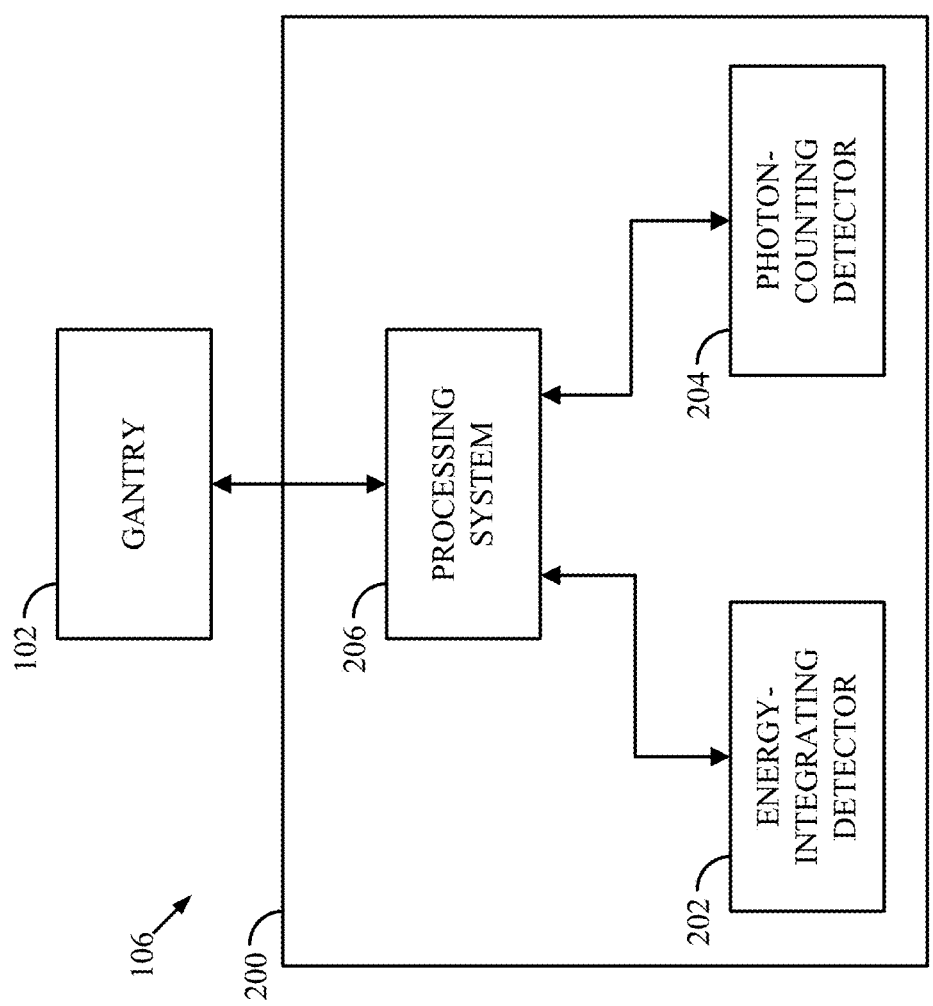
FIG. 2 is a schematic illustration of an example of a multi-detector system for use with the imaging system of FIG. 1.

FIG. 2 shows a schematic illustration of an example of a multi-detector system 200 of the detector assembly 106. The multi-detector system 200 forms part of the x-ray detection system 106. It can include a dedicated processing system 206 that may be in communication with the data-acquisition system 144, or the processing functionality of the processing system 206 can be integrated into the data-acquisition system 144, such as providing computer code to achieve the functionality described herein. The multi-detector system 200 includes an energy-integrating x-ray detector 202 that can sense x-rays emitted from the x-ray source assembly 104 in the energy integrated manner, such as in the form of a FPD. The multi-detector system 200 can also include a photon-counting detector assembly or system 204 configured to sense x-rays emitted from the x-source assembly 104 and determine individual x-ray photons and their corresponding energies, described above as a PCD system. In this way, the multi-detector system includes both an energy-integrating detector 202 and the photon-counting detector 204 that, together, are configured to receive the x-rays emitted from the x-ray source simultaneously.

Figure 3A:
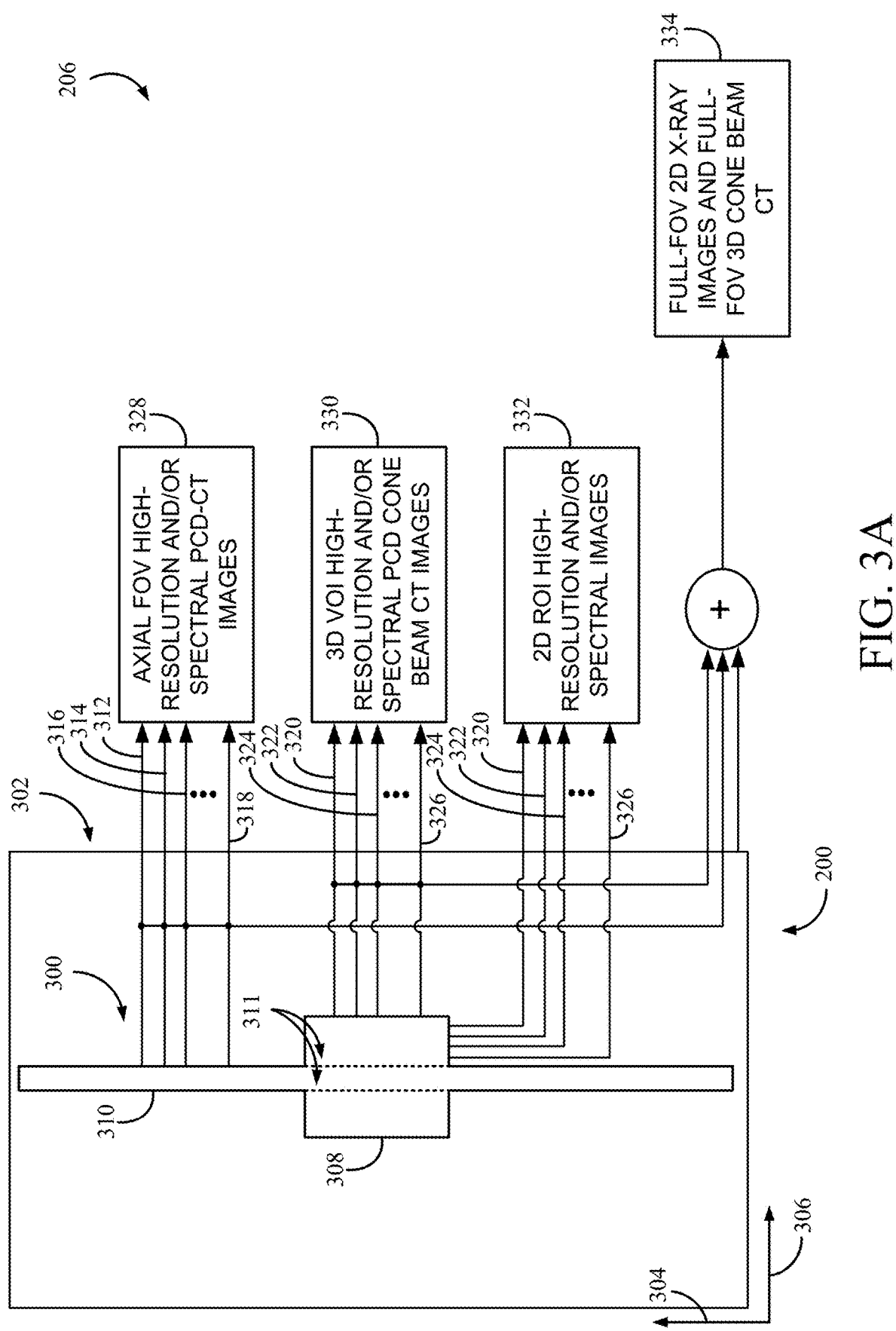
FIG. 3A is a schematic illustration of a multi-detector system in accordance with the present disclosure and configured for use with the systems of FIGS. 1 and 2.
Figure 3B:
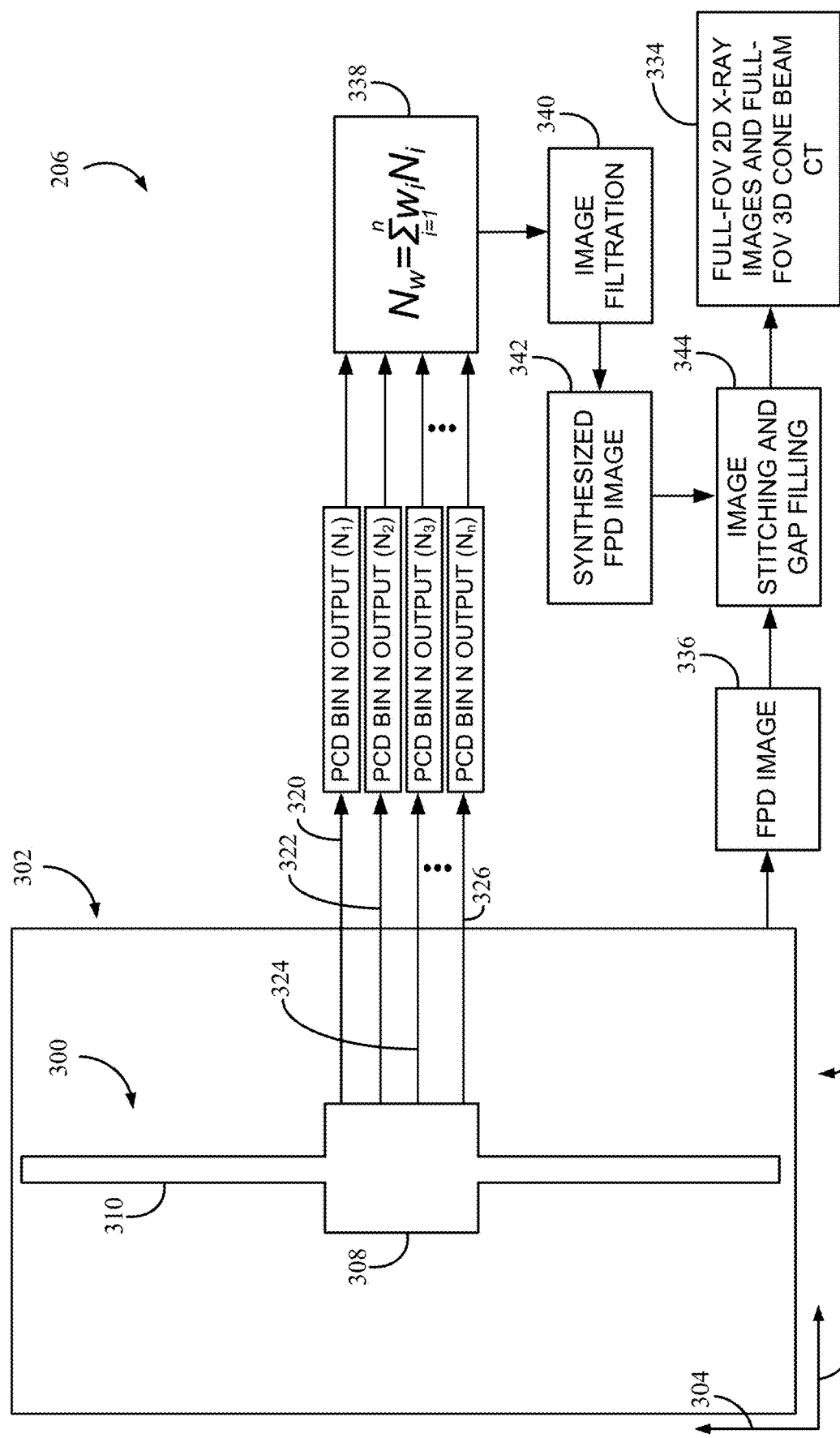
FIG. 3B is another schematic illustration of a multi-detector system in accordance with the present disclosure, including processing modules for creating any of a variety of images.

In some non-limiting examples, the detectors 202, 204 are integrated and coupled to a gantry of a CT system 102, such as the end of the C-arm 106, or a traditional diagnostic CT system. In one non-limiting example, the multi-detector system 200 may be formed as illustrated in FIGS. 3A-3B. In particular, one non-limiting example in accordance with the present disclosure combines a PCD module 300 with a FPD module 302. The FPD module 302 extends as a panel, for example, in an x-y plane 304 and a z-direction 306. In this way, it generally preserves the detector array and field of view (FOV), and functionality of traditional FPDs. Arranged over or integrated with the FPD module 302 the PCD module 300 to define a detecting area of the multi-detector system 200. Both the FPD module 302 the PCD module 300 can acquire x-rays simultaneously. This configuration advantageously reduces the overall system cost compared to a system that completely replaces foregoes an FPD in favor of a large-area PCD. That is, the PCD module 300 is designed to have a detector array that is constrained to a predetermined geometry that covers less physical area than the FPD module 302.

The PCD module 300 and FPD module 302 may have different shapes from each other. In one, non-limiting example illustrated in FIG. 3A, the FPD module 302 is a rectangle and the PCD module 300 is formed from a first submodule 308 and a second submodule 310. In the illustrated, non-limiting example, the first submodule 308 forms a rectangle intersecting with the second submodule 310, which is formed as an elongated strip. In this way, the illustrated the PCD module 302 may for a "dagger" shape, or any of a variety of other shapes. In this dagger shape, the PCD module 302 may be formed of two separate detector arrays, where a first is rectangular-shaped and a second is strip-shaped or "I" shaped. Alternatively, these two submodules 308, 310 may be integrated to form a single array of detectors forming the dagger shape or another shape. As illustrated by hidden lines 311, the "I" shape may be formed by one detector array sandwiched between two rectangular detector arrays arranged on either side of the "I" shape to form the rectangular shape. Alternatively, the "dagger" shape (or other shape) may be formed by one functional detector array, such as illustrated in FIG. 3B, where the hidden lines 311 are removed.

Though the specific geometries of the PCD module 300 and the FPD module 302 may be selected based on imaging preferences or clinical applications, this "dagger" shape can be advantageous because the second submodule 310 forming the strip provides data for full axial FOV for spectral and ultrahigh-resolution PCD-CT imaging at a given longitudinal location in the z-direction 306. The first submodule 308 forming the rectangle provides data for volume-of-interest (VOI) 3D and region-of-interest (ROI) 2D spectral and ultra-high-resolution imaging. Locations of the VOI and ROI can be selected by the treating physicians based on the full FOV CBCT or fluoroscopic images.

Other geometries or numbers of submodules 308, 310 are also possible. For example, instead of a rectangle, other shapes may be used, including squares, circles, ovals, or any of a variety of polygons or other shapes. Furthermore, instead of an elongated strip, a variety of dispersed modules may be arranged transversely to the first geometry or across the FPD module 302.

Regardless of the shapes or manner of integration utilized, the PCD module 300 may be integrated with the scintillator-based energy integrating FPD module 302 to form a single overall multi-detector or hybrid FPD-PCD detector. The PCD module 300 and FPD module 302 may be integrated in any of a variety of configurations. For example, the PCD module 300 may be inset within the FPD module 302, such that the FPD module 302 surrounds the sensing elements of the PCD module 300, to create a flush surface akin to a standard FPD detector panel. In this way, the PCD module 300 and the FPD module 302, together, form a continuous detector surface. That is, a single continuous surface may extend along the x-y plane 304 and the z-direction 306. In this way, no additional bulk or larger overall profile is created by the multi-detector system 200, as compared to a traditional, single-detector FPD detector panel. Alternatively, the PCD module 300 may be mounted over the FPD module 302.

Irrespective of particular geometries or configurations, when the full FOV of the FPD module 302 is required, the data provided by the PCD module 300 can be processed to form a seamless whole image together with the data provided by the FPD module 302. The PCD module 300 and FPD module 302 can share electronics system, as will be described with respect to FIG. 3B. For example, the PCD module 300 and FPD module 302 can utilize a shared electronics board.

Alternatively, the PCD module 300 can be mounted in front of the existing FPD, and a motorized device can be used to translate the PCD module 300 out of the FOV for the C-arm system to return to conventional FPD-based imaging modes. In this case, during an IGI process, when a clinical scenario requires spectral or high-resolution 3D or 2D imaging, the PCD module 300 can be automatically translated into the FOV.

The output data of the PCD module 300 can be used to create any of a variety of images. The data output of the PCD module 300 can be conceptualized as a series of data outputs corresponding to a series of energy bins. That is, as one non-limiting example, the output of the PCD module 300 can include raw counts associated with each of a plurality of energy bins. Moreover, the data from the first submodule 308 can be processed separately from the data from the second submodule 310, or the two can be processed together. In this regard, the data from each submodule 308, 310 of the PCD module 300 can be represented as a series of energy bins, from energy bin "1" 312, 320, to energy bin "2" 314, 322, to energy bin "3" 316, 324, through energy bin "n" 318, 326. The data from second submodule 310 of the PCD module 300 can be used to reconstruct an axial FOV high-resolution image and/or a spectral image 328. The output from the first submodule 308 of the PCD module 300 can be used to reconstruct 3D volumes of interest (VOI) with high resolution and/or spectral PCD cone beam CT images. Additionally, the output from the first submodule 308 of the PCD module 300 can be used to reconstruct 2D high-resolution and/or spectral images 332. Furthermore, the data from the first and second submodules 308, 310 of the PCD module 300 can be combined with the data from the FPD module 302. With the combined data, full-FOV 2D x-ray images and/or full-FOV 3D cone Beam CT data 334 can be reconstructed.

Referring to FIG. 3B, data from the multi-detector system 200 can be selective combined. In one example, data from the PCD module 300 can be combined with the output data of the scintillator-based energy integrating FPD module 302 to form, for example, a single full-FOV whole image. Likewise the output data of the scintillator-based energy integrating FPD module 302 can be used independently 336 or can be combined with additional data, as descried by the operator or dictated by the clinical application, as will be described.

Data associated with each energy bin 320-326 of the PCD module 300 can be weighted by the respective energy of the bin 338. That is, the energy-weighted data of different bins can be weighted and summed or otherwise combined together. The weighting factors of each energy bin can be calculated, experimentally calibrated, empirically (heuristically) determined, or assigned based on theory, unlike a data from the FPD module 302, which is not binned. To compensate for mismatched spatial resolution between the PCD module 300 and the FPD module 302, weighted image assembled from the data form the PCD module 300 can be filtered 340 until, for example, the spatial resolution and image textures match that of the FPD module 302 or another user-selected criteria to create a synthesized FPD image 342. Parameter(s) of the filter 340 can be determined theoretically, experimentally, or empirically (heuristically).

Through this process, the data from the PCD module 300 can be combed with the data from the FPD module 302 to form a seamless whole image 334, where any physical gaps, if there are any, can be compensated via digitally interpolating or stitching the gaps 344 using images 336 of the FPD module 302 and the PCD module 300. Thus, full-FOV 2D x-ray images and/or full-FOV 3D cone beam CT images can be produced despite the fact that multi-detector system 200 covers the full-FOV using two modules 300, 302 that are of different types/resolutions. Additionally or alternatively, dual imaging subtraction can be performed to create a mask image without the need for a separate mask image scan.

EXPERIMENTS

In one non-limiting example of a system created using the geometry illustrated in FIG. 3, a 51×0.6 cm$^2$ submodule 310 forming a strip was combined with a 5×10 cm$^2$ submodule 308 forming a rectangle that, together, formed the PCD module 300. The PCD module 300 was mounted on a C-arm gantry over the FPD module 302 to acquire preliminary experimental results as a proof-of-concept for the dagger PCD design and to demonstrate the potential benefits of 2D and 3D PCD imaging in IGIs.

The prototype formed a multi-detector system (FPD and PCD) constructed based on a Siemens Artis Zee interventional x-ray system C-arm gantry. The original C-arm system has a 40 cm×30 cm CsI:Tl FPD with 14-bit analog-to-digital converter (ADC) and 154 μm pixels. When operated under the CBCT imaging model, pixels of the FPD were binned (e.g., 4×4) to meet the frame rate requirement. The two PCD submodules were attached to the gantry separately using customized mounting devices. Both PCDs were manufactured by DirectConversion AB, Sweden: where the strip-shaped submodule was a XC-Hydra FX50 with a 0.75 mm layer of cadmium telluride (CdTe) as the x-ray sensor and a maximal readout frame rate of 150 fps. The rectangular-shaped submodule was Thor FX10 with 2 mm of CdTe and a maximal frame rate of 1000 fps. Both PCDs had two adjustable energy thresholds, 100% pixel fill factor, and 100 μm pixels. Unlike in MDCT, the x-ray tube in the interventional system was operated under the pulsed x-ray mode. Therefore, a synchronization between each PCD readout and each x-ray pulse was needed. This was achieved by feeding the "X-ray On" signal from the high voltage generator of the Siemens system to the trigger input of each PCD.

It is well known that the C-arm gantries wobble during rotation, and the C-arm with the mounted PCD module was no exception. Based on experimental data, the addition of the PCD to the C-arm gantry did not introduce any additional mechanical deformation. All observed geometric distortion came from the mechanical deformation of the original C-arm gantry. To correct for the wobbling-induced artifacts in the PCD-CT images, two customized geometric calibration phantoms were used.

The first one was for the geometric calibration of the rectangular submodule. It was similar to the so-called helix phantom commonly used for the geometric calibration of FPD-based CBCT, except much smaller, with a diameter of only 3 cm and a length of 5 cm to fit in the limited axial FOV of the rectangular PCD submodule footprint. It contained 41 steel bearing balls (BBs) arranged along a helical trajectory with an angular increment of 30 and a z-pitch of 1.27 mm.

The second geometric calibration phantom was used for the strip-shaped submodule. Due to the narrow z-coverage of the strip-shaped PCD submodule, helix phantoms were not applicable because no more than one BB can be seen by the submodule. Therefore, 11 BBs in a second phantom were arranged in the same axial plane. The coplanar design ensured all 11 BBs would show up on each projection image captured by the strip-shaped submodule For each PCD submodule and calibration phantom, a PCD-CT scan was performed and the projection matrices were estimated for each angle. During image reconstruction, the projection matrices were applied in the pixel-driven backprojection step. Phantom and in vivo animal experiments were performed to evaluate the 2D and 3D imaging performance of the two PCD submodules. The first image object was a 16 cm acrylic phantom that contains six inserts. Four inserts contained iodine with concentrations ranging from 10 to 20 mg/ml. The remaining two inserts contained 100 mg/ml and 200 mg/ml calcium (Ca).

In 125 kV FPD-CBCT images of this phantom, the 100 mg/ml Ca insert and the 10 mg/ml iodine insert demonstrated the same CT number of 322±20 HU. To address this "HU-degeneracy" problem, the strip-shaped submodule was used to acquired full axial FOV dual-energy PCD-CT images with the two energy thresholds of the PCD set to 15 and 63 keV. The recorded PCD images used 4×4 pixel binning. After the geometric correction, a PCD nonuniformity correction method was applied to both the low-energy (LE) and high-energy (HE) bin images, and then an image-domain material decomposition was performed to generate iodine basis images, virtual non-contrast images, and effective Z images using the HU ratio between the LE and HE images to differentiate between iodine and Ca inserts. The nonuniformity correction method is described in M. Feng, X. Ji, R. Zhang, K. Treb, A. M. Dingle, and K. Li, "An experimental method to correct low-frequency concentric artifacts in photon counting CT," Phys. Med. Biol., Vol. 66, pp. 175011, 2021., which is incorporated herein by reference in its entirety.

To demonstrate the spatial resolution benefits of the PCD, the strip-shaped submodule was used to scan an anthropomorphic head phantom that contains iodinated cerebral vessel models. The PCD was operated under an ultra-high resolution (UHD) mode, in which no binning was applied to the native 100 μm pixels, and a high-resolution reconstruction kernel was used for to generate UHD images. The UHD-mode acquisition was also applied to a Catphan phantom and an adult farm pig (53 kg) in vivo. To demonstrate the capability and benefits of VOI PCD-CT imaging using the rectangular-shaped submodule, a 3.5 mm stent with a kinked section was scanned by both UHD PCD-CT and FPD-CBCT. All acquisitions were performed at 125 kV, 7 s rotation speed, with 494 projection views that cover an angular span of 200, and 0.15 μGy per frame, and were reconstructed with a conventional filtered backprojection (FBP) algorithm with the Parker short scan weighting. Except for the pig study and stent images, all FPD-CBCT acquisitions used a narrow (2.5 cm) collimation along the z-direction.

Figure 4:
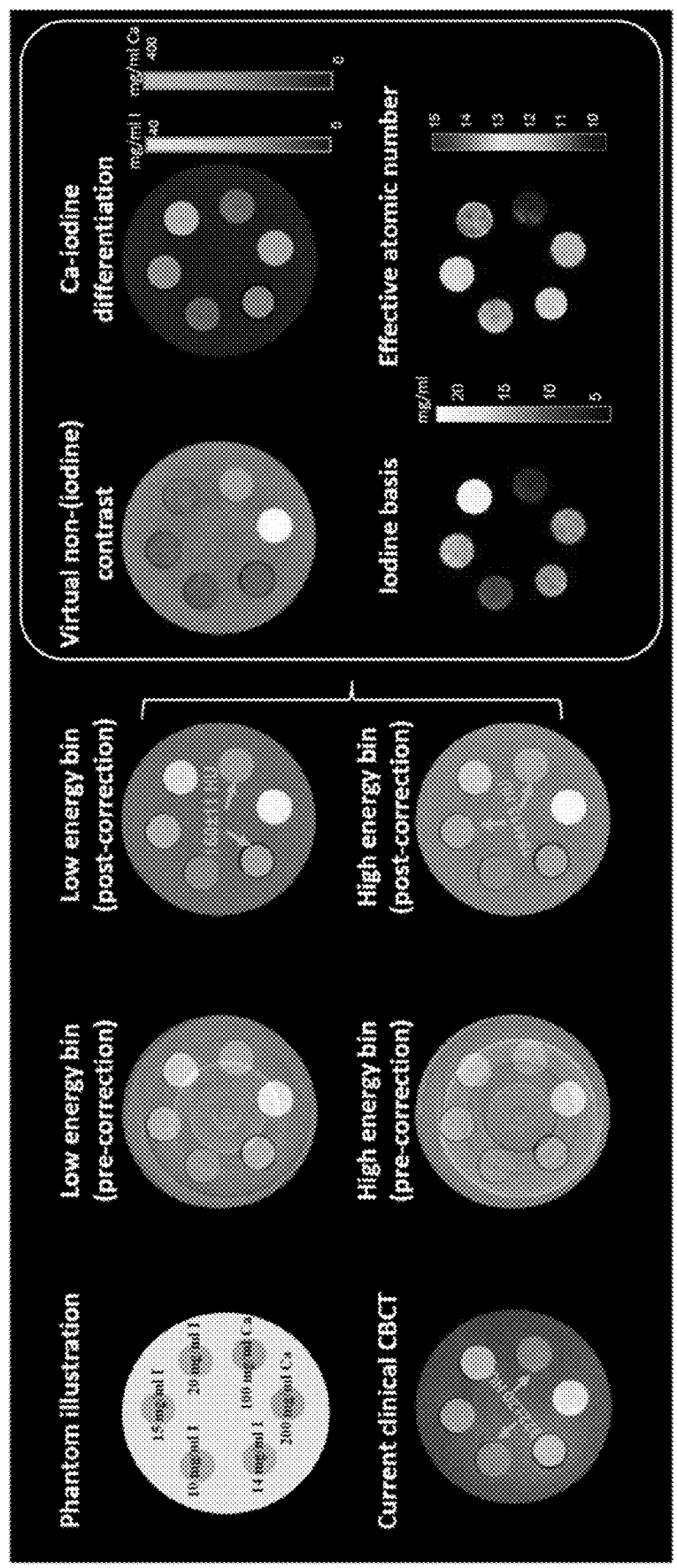
FIG. 4 is a set of correlated images of a phantom acquired using one, non-limiting example system accordance with the present disclosure.
Figure 5:
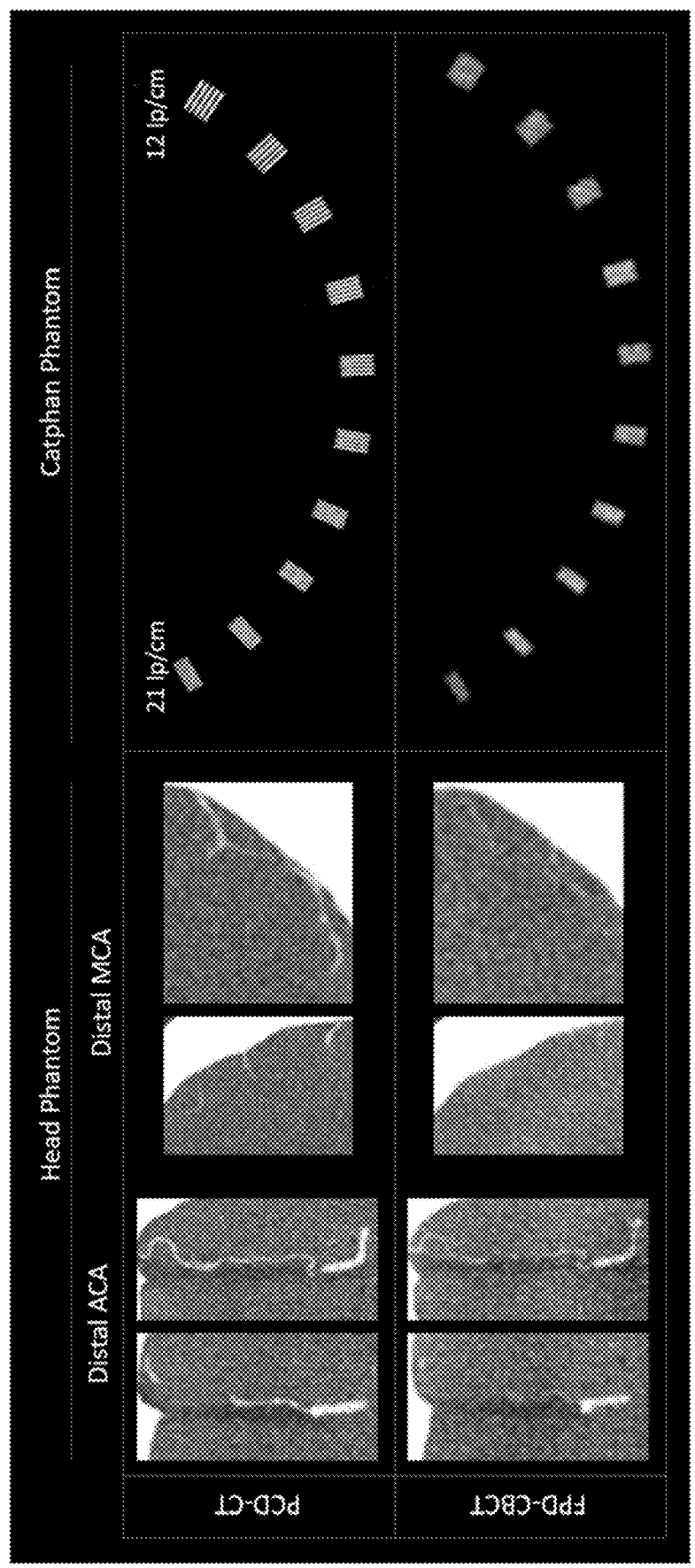
FIG. 5 is a set of correlated images of two phantoms acquired using one, non-limiting example system accordance with the present disclosure.

FIG. 4 is a set of correlated phantom PCD-CT images of the 16 cm phantom acquired using the strip-shaped submodule operated under the dual-energy mode. With the detector non-uniformity correction method developed in Feng et al. directly referenced above, high-quality and ring artifact-free PCD-CT images were generated for the LE and HE bins, which were used to generate material basis and other quantitative images that can differentiate inserts with the same CT number in the FPD-CBCT image. FIG. 5 provides a correlated series of images of an anthropomorphic head phantom and the Catphan600 phantom. More particularly, FIG. 5 compares FPD-CBCT images with PCD-CT images acquired using the strip-shaped submodule operated under UHD mode. As can be seen in FIG. 5, for the head phantom results, distal cerebral vessels were completely or partial missed on FPD-CBCT images, but were clearly visualized on C-arm PCD-CT images. When all distal and smaller artery branches (0.5 mm) are considered, the CNR was 6.9 [95% CI: 5.8, 8.0] in PCD-CT and 2.9 [95% CI: 2.1, 3.7] in FPD-CBCT.

Figure 6:
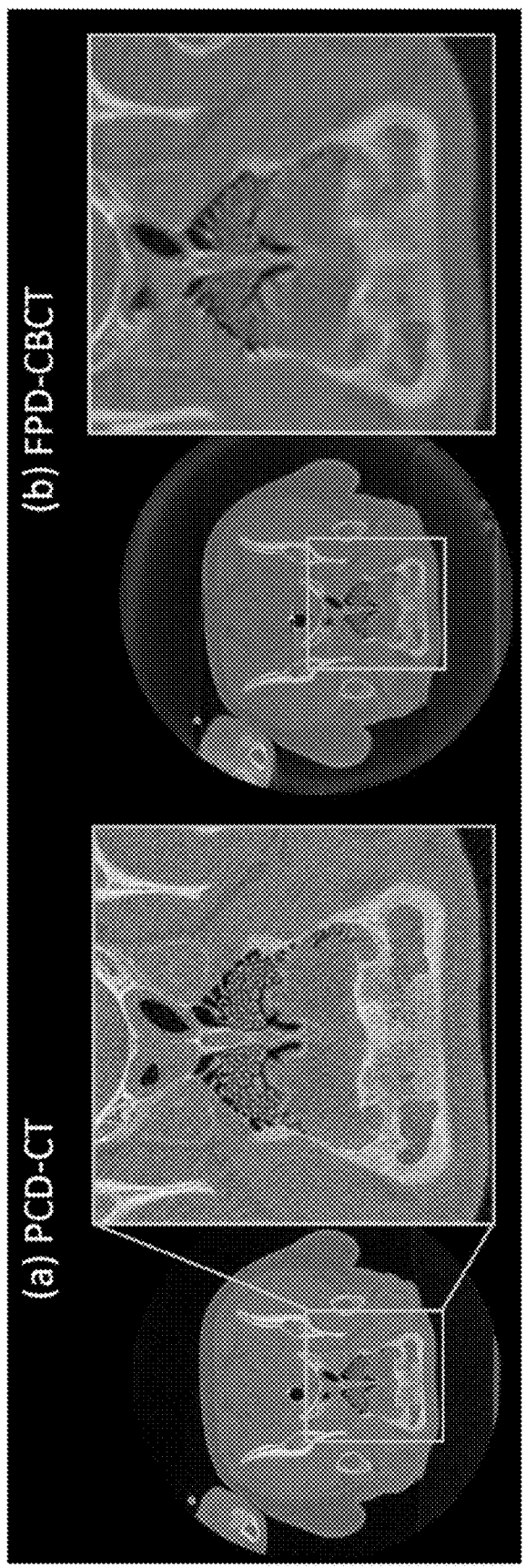
FIG. 6 is a set of correlated images of a pig acquired using one, non-limiting example system accordance with the present disclosure.
Figure 7:
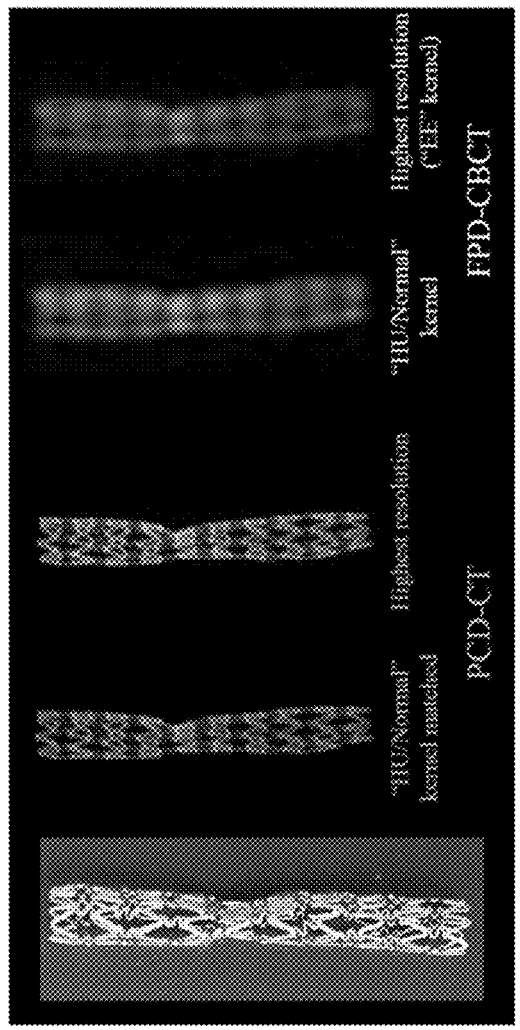
FIG. 7 is a set of correlated images of a stent acquired using one, non-limiting example system accordance with the present disclosure.

The improved small vessel visualization is due to the intrinsically superior spatial resolution of the PCD. As further shown in FIG. 5 by the Catphan images, the UHD PCD-CT was able to resolve the finest line pair pattern (21 lp/cm), compared with the 12 lp/cm limiting spatial resolution of FPD-CBCT. The in vivo pig images shown in FIG. 6 is a set of images of a pig. FIG. 6 demonstrated a similar spatial resolution benefit of PCD-CT. With the proposed geometric calibration and detector non-uniformity corrections, no distortions or ring artifacts can be observed in the PCD-CT images. FIG. 7 shows PCD-CT VOI images acquired using the rectangular-shaped module operated under UHD mode. Both FPD-CBCT and PCD-CT images were acquired with matched beam collimation and matched radiation dose. The images were reconstructed with a matched isotropic voxel size of 0.07 mm. Even when the reconstruction kernel is matched between the PCD-CT and FPD-CBCT, the UHD PCD-CT shows the stent much more clearly and with better resolution. When the high-resolution capabilities of the PCD-CT and FPD-CBCT are pushed to their limits with the sharper kernels, the FPD-CBCT again fails to resolve the stent as clearly as the PCD-CT.

In summary, the multi-detector FPD-PCD system described herein can be used to upgrade existing C-arm interventional x-ray systems or create new systems. In either case, the systems and methods provided herein provide spectral and ultra-high resolution capabilities, and also have been experimentally demonstrated from using prototypes. The results confirmed multiple advantages of PCD-based IGIs. For example, spectral and quantitative imaging is available to help resolve ambiguous findings during procedures. As another example, ultra-high spatial resolution can be used to help resolve small perforating blood vessels and interventional devices. The particular geometry used in the experiments described herein that includes a strip-shaped submodule and a rectangular-shaped submodule combining to form the PCD, demonstrate mutually complementary designs, particularly, when mounted on or combined with a FPD. The system provides superior flexibility such that the system can operate to provide traditional FPD images, or can provide improved resolution, multi-spectral capabilities, or other functionality, each of which can be chosen by physicians based on the specific clinical needs. That is, the systems and methods provide, for example, 1) spectral imaging capability; 2) much superior soft-tissue contrast detectability; 3) much higher spatial resolution, compared to traditional FPD systems. Furthermore, the system does not include complex mechanical structures or moving parts. Rather, it can be selectively controlled by the operator and the processing system, for example using electronic switching and or data processing.

Although some of the discussion above is framed in particular around systems, such as the various isolation system, those of skill in the art will recognize therein an inherent disclosure of corresponding methods of use (or operation) of the disclosed systems, and the methods of installing the disclosed systems. Correspondingly, some non-limiting examples of the disclosure can include methods of using, making, and installing isolation systems.

Although the invention has been described and illustrated in the foregoing illustrative non-limiting examples, it is understood that the present disclosure has been made only by way of example, and that numerous changes in the details of implementation of the invention can be made without departing from the spirit and scope of the invention, which is limited only by the claims that follow. Features of the disclosed non-limiting examples can be combined and rearranged in various ways.

Furthermore, the non-limiting examples of the disclosure provided herein are not limited in application to the details of construction and the arrangement of components set forth in the following description or illustrated in the following drawings. The invention is capable of other non-limiting examples and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," ""connected," "supported," and "coupled" and variations thereof are used broadly and encompass both direct and indirect mountings, connections, supports, and couplings. Further, "connected"and "coupled" are not restricted to physical or mechanical connections or couplings.

Also, the use the phraseology and terminology used herein is for the purpose of description and should not be regarded as limiting. The use of "right", "left", "front", "back", "upper", "lower", "above", "below", "top", or "bottom" and variations thereof herein is for the purpose of description and should not be regarded as limiting. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

Unless otherwise specified or limited, phrases similar to "at least one of A, B, and C,""one or more of A, B, and C," etc., are meant to indicate A, or B, or C, or any combination of A, B, and/or C, including combinations with multiple or single instances of A, B, and/or C.

In some non-limiting examples, aspects of the present disclosure, including computerized implementations of methods, can be implemented as a system, method, apparatus, or article of manufacture using standard programming or engineering techniques to produce software, firmware, hardware, or any combination thereof to control a processor device, a computer (e.g., a processor device operatively coupled to a memory), or another electronically operated controller to implement aspects detailed herein. Accordingly, for example, non-limiting examples of the invention can be implemented as a set of instructions, tangibly embodied on a non-transitory computer-readable media, such that a processor device can implement the instructions based upon reading the instructions from the computer-readable media. Some non-limiting examples of the invention can include (or utilize) a device such as an automation device, a special purpose or general purpose computer including various computer hardware, software, firmware, and so on, consistent with the discussion below.

The term "article of manufacture" as used herein is intended to encompass a computer program accessible from any computer-readable device, carrier (e.g., non-transitory signals), or media (e.g., non-transitory media). For example, computer-readable media can include but are not limited to magnetic storage devices (e.g., hard disk, floppy disk, magnetic strips, and so on), optical disks (e.g., compact disk (CD), digital versatile disk (DVD), and so on), smart cards, and flash memory devices (e.g., card, stick, and so on). Additionally, it should be appreciated that a carrier wave can be employed to carry computer-readable electronic data such as those used in transmitting and receiving electronic mail or in accessing a network such as the Internet or a local area network (LAN). Those skilled in the art will recognize many modifications may be made to these configurations without departing from the scope or spirit of the claimed subject matter.

Certain operations of methods according to the invention, or of systems executing those methods, may be represented schematically in the FIGS. or otherwise discussed herein. Unless otherwise specified or limited, representation in the FIGS. of particular operations in particular spatial order may not necessarily require those operations to be executed in a particular sequence corresponding to the particular spatial order. Correspondingly, certain operations represented in the FIGS., or otherwise disclosed herein, can be executed in different orders than are expressly illustrated or described, as appropriate for particular non-limiting examples of the invention. Further, in some non-limiting examples, certain operations can be executed in parallel, including by dedicated parallel processing devices, or separate computing devices configured to interoperate as part of a large system.

As used herein in the context of computer implementation, unless otherwise specified or limited, the terms "component," "system," "module," etc. are intended to encompass part or all of computer-related systems that include hardware, software, a combination of hardware and software, or software in execution. For example, a component may be, but is not limited to being, a processor device, a process being executed (or executable) by a processor device, an object, an executable, a thread of execution, a computer program, or a computer. By way of illustration, both an application running on a computer and the computer can be a component. One or more components (or system, module, and so on) may reside within a process or thread of execution, may be localized on one computer, may be distributed between two or more computers or other processor devices, or may be included within another component (or system, module, and so on).

As used herein, the term, "controller" and "processor" and "computer" include any device capable of executing a computer program, or any device that includes logic gates configured to execute the described functionality. For example, this may include a processor, a microcontroller, a field-programmable gate array, a programmable logic controller, etc. As another example, these terms may include one or more processors and memories and/or one or more programmable hardware elements, such as any of types of processors, CPUs, microcontrollers, digital signal processors, or other devices capable of executing software instructions.

The invention claimed is:

1. An x-ray imaging system comprising:
a gantry configured rotate about a pivot axis;
an x-ray source coupled to the gantry and configured to emit x-rays along a path extending to define an axial axis; and
an x-ray detector system coupled to the gantry and configured to receive x-rays traveling from the x-ray source along the path, wherein the x-ray detector system includes:
an energy-integrating x-ray detector having an array of energy-integrating x-ray sensors that are configured to sense x-rays emitted from the x-ray source;
a photon-counting detector having another array of photon-counting x-ray sensors configured to determine an interaction between individual x-ray photons from the x-ray source and individual photon-counting x-ray sensors;
wherein both the energy-integrating detector and the photon-counting detector are configured to receive the x-rays emitted from the x-ray source simultaneously; and
wherein the energy-integrating x-ray sensors define a first shape and the photon-counting x-ray sensors define a second shape, wherein the first shape is a first rectangle having a space formed therein to receive the second shape, wherein the second shape is an elongated strip intersecting a second rectangle, wherein a width of the second rectangle is greater than a width of the elongated strip and a length of the second rectangle is smaller than a length of the elongated strip.

2. The system of claim 1, wherein the array of energy-integrating x-ray sensors of the energy-integrating x-ray detector defines a first sensing area, wherein the array of photon-counting x-ray sensor of the photon-counting detector defines a second sensing area, and wherein the first sensing area and the second sensing area, together, define a detecting area of the x-ray detector system.

3. The system of claim 1, wherein the array of energy-integrating x-ray sensors of the energy-integrating x-ray detector and the array of photon-counting x-ray sensors of the photon-counting detector, together, form a continuous detector surface of the x-ray detector system.

4. The system of claim 1, wherein the array of energy-integrating x-ray sensors of the energy-integrating x-ray detector surround the array of photon-counting x-ray sensors of the photon-counting detector.

5. The system of claim 1, wherein the energy-integrating detector and the photon-counting detector share processing electronics.

6. The system of claim 1, wherein data from the energy-integrating detector and data from the photon-counting detector share are integrated to form an image of a subject arranged in the path.

7. The system of claim 6, further comprising a processing system configured to receive data from the energy-integrating detector and data from the photon-counting detector and reconstruct at least one of:
   an axial image;
   a spectral image;
   a two-dimensional region-of-interest image;
   a three-dimensional image;
   a spectral cone-beam image; or
   a full field-of-view image.

8. The system of claim 7, wherein the processing system is configured to reconstruct the full field-of-view image by combining data from the energy-integrating detector and data from the photon-counting detector.

9. The system of claim 8, wherein the processing system is configured to combine data from the energy-integrating detector and data from the photon-counting detector by:
   weighting the data from the photon-counting detector by an energy bin to create a weighted image;
   apply an image filtration to the weighted image to create a synthesized flat-panel detector image;
   reconstruct a flat-panel detector image using the data from the energy-integrating detector;
   perform stitching and gap filling to integrate the synthesized flat-panel detector image with the flat-panel detector image.

10. The system of claim 1, wherein the photon-counting detector is inset within the energy-integrating detector to form a single detector panel.

11. A method of controlling an x-ray imaging system including a gantry, an x-ray source coupled to the gantry, and a multi-detector assembly having an energy-integrating detector array and a photon-counting detector array, the method comprising:
   operating the x-ray source to direct x-rays to the multi-detector assembly;
   acquiring energy-integrating x-ray imaging data in response to receiving the x-rays at the energy-integrating detector array;
   simultaneously with receiving the x-rays at the energy-integrating detector array, acquiring photon-counting x-ray imaging data in response to receiving the x-rays at the photon-counting detector array; and
   reconstructing an image of the subject using at least one of the energy-integrating x-ray imaging data or the photon-counting x-ray imaging data;
   wherein the energy-integrating detector array defines a first shape and the photon-counting detector array defines a second shape, wherein the first shape is a first rectangle having a space formed therein to receive the second shape, wherein the second shape is an elongated strip intersecting a second rectangle, wherein a width of the second rectangle is greater than a width of the elongated strip and a length of the second rectangle is smaller than a length of the elongated strip.

12. The method of claim 11, wherein reconstructing the image includes:
   weighting the photon-counting x-ray data by an energy bin to create a weighted image;
   apply an image filtration to the weighted image to create a synthesized flat-panel detector image;
   reconstruct a flat-panel detector image using the energy-integrating x-ray imaging data;
   perform stitching and gap filling to integrate the synthesized flat-panel detector image with the flat-panel detector image.

13. The method of claim 11, further comprising selecting between selecting at least one of:
   an axial image;
   a spectral image;
   a two-dimensional region-of-interest image;
   a three-dimensional image;
   a spectral cone-beam image; or
   a full field-of-view image.

14. An x-ray detector system comprising:
   an energy-integrating x-ray detector having an array of energy-integrating x-ray sensors that are configured to sense x-rays emitted from an x-ray source and generate energy-integrating x-ray data;
   a photon-counting detector having another array of photon-counting x-ray sensors configured to determine an interaction between individual x-ray photons with individual photon-counting x-ray sensors to generate photon-counting x-ray data;
   electronics configured to receive the energy-integrating x-ray data and the photon-counting x-ray data simultaneously; and
   wherein the energy-integrating x-ray sensors define a first shape and the photon-counting x-ray sensors define a second shape, wherein the first shape is a first rectangle having a space formed therein to receive the second shape, wherein the second shape is an elongated strip intersecting a second rectangle, wherein a width of the second rectangle is greater than a width of the elongated strip and a length of the second rectangle is smaller than a length of the elongated strip.

15. The system of claim 14, wherein the photon-counting detector is inset with in the energy-integrating detector to form an integrated detector panel.

* * * * *